United States Patent [19]

Effenberger et al.

[11] 4,234,744
[45] Nov. 18, 1980

[54] PROCESS FOR THE PRODUCTION OF AMINOACID HYDROCHLORIDES/OR DIAMINOACID DIHYDROCHLORIDES

[75] Inventors: Franz Effenberger, Stuttgart; Karlheinz Drauz, Heilbronn, both of Fed. Rep. of Germany

[73] Assignee: Deutsche Gold- und Silber Scheideanstalt vormals Roessler, Frankfurt, Fed. Rep. of Germany

[21] Appl. No.: 104,064

[22] Filed: Dec. 17, 1979

[30] Foreign Application Priority Data

Dec. 18, 1978 [DE] Fed. Rep. of Germany ....... 2854627

[51] Int. Cl.³ .............................................. C07C 99/00
[52] U.S. Cl. ..................... 562/562; 560/157;
560/158; 562/553; 562/561; 562/575; 562/576
[58] Field of Search ................ 560/157; 562/575, 553, 562/576, 561, 562

[56] References Cited

U.S. PATENT DOCUMENTS

| | | | |
|---|---|---|---|
| 2,647,916 | 8/1953 | Kaiser | 560/24 |
| 3,526,655 | 9/1970 | Argabright | 560/157 |
| 3,674,750 | 7/1972 | Brady | 560/157 |
| 4,147,716 | 4/1979 | Chung | 560/157 |

FOREIGN PATENT DOCUMENTS 42-3614 2/1967 Japan .

Primary Examiner—Natalie Trousof
Assistant Examiner—Michael Shippen
Attorney, Agent, or Firm—Cushman, Darby & Cushman

[57] ABSTRACT

Aminoacid hydrochlorides or diaminoacid dihydrochlorides are produced by first reacting a halocarboxylic acid ester with an alkali metal cyanate in the presence of an alcohol to form the corresponding mono- or diurethane and then saponifying this to the corresponding mono- or dihydrochloride. The new process is relatively versatile in its use and above all opens up an elegant synthesis route for lysine.

14 Claims, No Drawings

PROCESS FOR THE PRODUCTION OF AMINOACID HYDROCHLORIDES/OR DIAMINOACID DIHYDROCHLORIDES

BACKGROUND OF THE INVENTION

There are already known numerous processes for the production of aminoacids or their derivatives. In many of these known processes halocarboxylic acids serve as starting materials. In these cases the exchange of halogen for an amino group is the essential process step. As aminating agent there serve ammonia or ammonia derivatives such as potassium phthalimide, p-toluenesulfonamide or hexamethylenetetramine. The known processes are frequently well suited for the production of specific aminoacids but are less well suited or not at all suited for the production of other aminoacids. Particular problems occur if lysine is to be produced from 2,6-dihalohexanoic acids because then almost always there is formed exclusively or at least preponderantly pipecolic acid.

SUMMARY OF THE INVENTION

According to the invention there is provided a process for the production of aminoacid hydrochlorides or diaminoacid dihydrochlorides by reacting an ester of a halocarboxylic acid having the formula

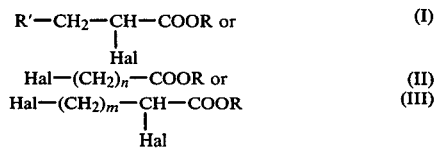

in which Hal is chlorine or bromine, R is methyl or ethyl, R' is hydrogen or a straight or branched chain alkyl group with 1 to 6 carbon atoms, n is one or a whole number between 3 and 5 inclusive and m is a whole number between 2 and 4 inclusive, in an aprotic solvent (inert in the reaction) at a temperature between 80 and 120° C. with an alkali metal cyanate of the formula MeOCN in which Me is lithium, sodium, or potassium, and methanol or ethanol and subsequently saponifying the alkoxycarbonylaminocarboxylic acid ester or bis-(alkoxy-carbonylamino)-carboxylic acid ester with a mixture of equal parts of concentrated hydrochloric acid, 100 weight percent formic acid and water at reflux temperature.

Examples of suitable starting esters include methyl 2-chloropropionate, methyl 2-bromopropionate, ethyl 2-chloropropionate, methyl 2-chlorobutyrate, ethyl 2-chlorobutyrate, methyl 2-chlorovalerate, ethyl 2-chlorovalerate, ethyl 2-bromovalerate, methyl 2-chlorocaproate, ethyl 2-chlorocaproate, methyl 2-bromocaproate, ethyl 2-bromocaproate, methyl 2-bromocaprylate, methyl 2-chlorocaprylate, ethyl 2-chlorocaprylate, methyl 2-chlorononanoate, ethyl 2-chlorononanoate, ethyl 2-bromononanoate, methyl 2-chloro-4-methylpentanoate, ethyl 2-chloro-4-methylpentanoate, ethyl 2-bromo-4-methylpentanoate, methyl chloroacetate, ethyl chloroacetate, methyl bromoacetate, ethyl bromoacetate, methyl 4-chlorobutyrate, ethyl 4-chlorobutyrate, methyl-4-bromobutyrate, ethyl 4-bromobutyrate, methyl 5-chlorovalerate, ethyl 5-chlorovalerate, methyl 6-chlorocaproate, ethyl 6-chlorocaproate, methyl 6-bromocaproate, methyl 2,4-dichlorobutyrate, ethyl 2,4-dichlorobutyrate, methyl 2,4-dibromobutyrate, ethyl 2,4-dibromobutyrate, methyl 2,5-dichlorovalerate, ethyl 2,5-dichlorovalerate, ethyl 2,5-dibromovalerate, methyl 2,6-dichlorocaproate, ethyl 2,6-dichlorocaproate, methyl 2,6-dibromocaproate, ethyl 2,6-dibromocaproate, methyl 2-bromo-6-chlorocaproate.

The process of the invention is relatively versatile in its use and in particular even permits the production of lysine from 2,6-dihalohexanoic acid esters.

The compounds of general formula I to III without exception are known materials which can be produced by known processes.

The reaction of these compounds with the alkali metal cyanate and the alcohol takes place in an aprotic solvent. Suitable solvents for example are acetonitrile and especially dimethyl sulfoxide, dimethylformamide and N-methyl pyrrolidone. Especially preferred is dimethylformamide.

As alkali metal cyanates there can be used lithium cyanate, sodium cyanate or potassium cyanate. Particularly preferred is potassium cyanate. It is suitably added in an amount of at least one mole per mole of reacting halo substituent. The use of an excess of 10 to 100%, preferably about 50% over the mentioned amount of cyanate is advantageous.

As alcohols there are used methanol or ethanol. Methanol is preferred. To avoid undesired side reactions it is suitable to use methanol in the reaction of halocarboxylic acid methyl esters and to use ethanol in the reaction of halocarboxylic acid ethyl esters. The alcohols are suitably used in an amount of at least one mole per mole of alkali metal cyanate added.

The use of an excess of 10 to 600%, preferably 125 to 250%, over the mentioned amount of alcohol is advantageous.

The reaction of the halocarboxylic acid ester with the alkali metal cyanate and alcohol takes place at a temperature between 80 and 120° C., preferably at about 100° C. In this reaction urethanes are formed directly. In fact the corresponding alkoxycarbonylaminocarboxylic acid esters ("monourethanes") are formed from compounds of general formulae I and II. The reaction of the compounds of general formula III can be so guided that there are formed the corresponding bis-(alkoxycarbonylamino)-carboxylic acid esters ("diurethanes"). In these cases it is suitable to start from either the dichloro or dibromo compounds. Special conditions are present in the reaction of the 2,5-dihalovaleric acid esters. Here obviously the intramolecular reaction to a five membered ring is so greatly favored based on energy reasons that besides the expected 2,5-bis-(alkoxycarbonylamino)-valeric acid esters there are also formed considerable amounts of N-alkoxycarbonylproline esters. On the other hand, however, the reaction of 2-bromo-ω-chlorocarboxylic acid esters of general formula III can also be so guided that an alkoxy carbonylamino group is introduced only in the 2-position, thus a monourethane is formed which in the ω-position still has a reactable chlorine atom.

To shorten the required reaction time it can be advantageous, if the reaction of the halocarboxylic acid ester with the alkali metal cyanate and the alcohol is carried out in the presence of a so-called phase transfer catalyst. Suitable phase transfer catalysts are crown ethers, quaternary ammonium salts, phosphonium salts and arsonium salts or copper complexes. Particularly suited are tetraethyl ammonium cyanate and hexamethyl guanidinium cyanate. For example they can be used in an amount of 5 to 10 mole percent based on the amount of halocarboxylic acid ester employed.

In general the reaction of the chlorocarboxylic acid esters clearly requires longer reaction times than the reaction of the corresponding bromocarboxylic acid esters. The reaction times, however, can be shortened considerably if there is added potassium bromide. Suitable amounts of potassium bromide are 0.5 to 1.5 moles, especially about 1 mole per mole of alkali metal cyanate added. There can also be used sodium bromide in place of potassium bromide.

The reaction time required for the reaction of chlorocarboxylic acid ester in dimethylformamide in the absence of potassium bromide is about 30 hours, in the presence of potassium bromide about 8 to 9 hours, the reaction time required for the reaction of bromocarboxylic acid esters in dimethylformamide is only about 0.5 to 7 hours.

The monourethane or diurethane formed in the reaction of the halocarboxylic acid ester with the alkali metal cyanate and alcohol can be subjected directly to the saponification. However, it is generally advantageous to isolate it in pure form and only then to undertake the saponification. The monourethanes can be purified through fractional distillation or through liquid chromatography while the diurethanes in general can only be purified through liquid chromatography. Ethyl acetate is particularly suited as the running agent in the liquid chromatography.

The crude or purified monourethane or diurethane is saponified with a mixture of equal parts by volume of concentrated hydrochloric acid, 100 parts by weight of formic acid and water. In the preparation of this mixture, however, naturally there must not be used water free formic acid. There can much more desirably be added aqueous, for example 85 weight percent, formic acid and the amount of water be reduced correspondingly. The saponification of the monourethane or diurethane generally requires about 24 hours of heating at reflux temperature. In the saponification simultaneously the alkoxy carbonyl groups and the ester groups are split off and the hydrochloride or dihydrochloride formed.

After the end of the saponification the acid mixture is suitably distilled under reduced pressure and the residue washed with acetone, to which in a given case small amounts of ethanol or diethyl ether can be added. If purified monourethane or diurethane is employed for the saponification then the corresponding aminoacid hydrochloride or diaminoacid dihydrochloride are present in fine crystalline form and are generally thin layer chromatographically pure. The free aminoacids or diaminoacids can be recovered from them in a given case in a manner known of itself, e.g. by means of an anion exchanger.

By the process of the invention there can be produced for example from compounds of general formula I the hydrochloride of alanine, α-aminobutyric acid, norleucine or leucine, from compounds of general formula II the hydrochloride of glycin, 4-aminobutyric acid or 6-aminohexanoic acid, from compounds of general formula III the dihydrochloride of 2,4-diaminobutyric acid, or ornithine or lysine as well as the hydrochloride of proline. The process of the invention is particularly valuable because it opens up a new and advantageous route for the production of lysine.

Unless otherwise indicated all parts and percentages are by weight. in the working examples the concentrated hydrochloric acid was about 36% by weight.

The process can comprise, consist essentially of or consist of the steps set forth and the composition employed can comprise, consist essentially of or consist of the materials set forth.

The process of the invention is more closely illustrated in the following examples:

DESCRIPTION OF THE PREFERRED EMBODIMENTS

EXAMPLE 1

14.63 grams of 2-bromohexanoic acid methyl ester, 8.52 grams of potassium cyanate and 7.85 grams of methanol were heated in 70 ml of dimethylformamide (DMF) at 100° C. for 45 minutes under vigorous stirring. After the cooling off of the reaction mixture the salts were filtered off and the filtrate concentrated in a vacuum. The viscous residue was taken up with 50 ml of acetone and the undissolved material filtered off. Subsequently the acetone was distilled off and the residue fractionated in the high vacuum. There resulted 10.75 grams (75.5%) of 2-methoxycarbonylaminohexanoic acid methyl ester having a boiling point of 78° C./0.007 mbar.

EXAMPLE 2

11.52 grams of 2-chlorohexanoic acid methyl ester were heated with 8.52 grams of potassium cyanate and 7.85 grams of methanol in 70 ml of DMF. After a reaction time of 30 hours the reaction mixture was worked up as described in Example 1. There were obtained 9.53 grams (67%) of 2-methoxycarbonylaminohexanoic acid methyl ester with a purity of 99% (determined gas chromatographically).

EXAMPLE 3

4.07 grams of 2-methoxycarbonylaminohexanoic acid methyl ester were heated in 15 ml of a mixture consisting of equal parts of concentrated hydrochloric acid, 100 weight percent formic acid and water for 24 hours under reflux. The acid mixture was removed in a vacuum, the oily residue treated twice with 20 ml of acetone and freed from acetone again in a vacuum. The now crystalline residue was intensively stirred with 10 ml of acetone, filtered with suction and dried over diphosphorus pentoxide. There were obtained 3.26 grams (97.3%) of D,L-norleucine hydrochloride pure by thin layer chromatography.

EXAMPLE 4

The reaction of 10.45 grams of 6-bromohexanoic acid methyl ester with 6.08 grams of potassium cyanate and 2.7 grams of methanol in 50 ml DMF following the procedure of Example 1 gave 7.82 grams (76.9%) of 6-methoxycarbonylaminohexanoic acid methyl ester having a boiling point of 104° C./0.0013 mbar.

EXAMPLE 5

In a manner corresponding to Example 2 there were reacted 11.52 grams of 6-chlorohexanoic acid methyl ester to form 9.89 grams (69.5%) 6-methoxycarbonylaminohexanoic acid methyl ester. This had a purity of 99% determined gas-chromatographically.

EXAMPLE 6

4.07 grams of 6-methoxycarbonylaminohexanoic acid methyl ester were saponified in the manner described in Example 3. There were obtained 3.14 grams (93.7%) of 6-aminohexanoic acid hydrochloride.

EXAMPLE 7

There were added to 2.88 grams of 2,6-dibromohexanoic acid methyl ester in 20 ml of N-methyl pyrrolidone 2.44 grams of potassium cyanate and 2.18 grams of methanol. This mixture was stirred for 60 minutes at 120° C. Gas chromatographically there was detected a degree of conversion of 66.7% to 2,6-bis(methoxycarbonylamino)-hexanoic acid methyl ester. After cooling the reaction mixture, the salt was separated off and washed with chloroform. The filtrate and wash solution were concentrated together in a high vacuum at 95° C. There were added to the oily residue 25 ml each of acetone and ether and the residual salt filtered off with suction. After the removal of the solvent there remained 8 ml of a highly viscous orange oil which was purified by liquid chromatography with ethyl acetate (silica gel column, Type C, 40×4.0 cm with silica gel Merck 0.015–0.025 mm).

There were obtained in two fractions altogether 1.70 grams (61.4%) of pure 2,6-bis(methoxycarbonylamino)-hexanoic acid methyl ester.

The saponification took place with 42 ml of the mixture of concentrated hydrochloric acid/100 weight percent formic acid/water in the manner of Example 3 and yielded 1.127 grams (51.5% based on the 2,6-dibromohexanoic acid methyl ester) of D,L-lysine dihydrochloride with a melting point of 187°–189° C. which is pure by thin layer chromatography.

EXAMPLE 8

In the reaction of 1.99 grams of 2,6-dichlorohexanoic acid methyl ester with 2.44 grams of potassium cyanate and 3.27 grams of methanol there were formed in the presence of 3.57 grams of potassium bromide after a reaction time of 8 hours at 120° C. in 20 ml N-methyl pyrrolidone 1.25 grams (45.3%) of 2,6-bis(methoxycarbonylamino)-hexanoic acid methyl ester. To isolate and saponify to D,L-lysine dihydrochloride there was employed the procedure of Example 7.

EXAMPLE 9

From the reaction of 11.69 grams of 2-bromopropionic acid methyl ester with 8.52 grams of potassium cyanate and 7.85 grams of methanol under the conditions described in Example 1 there were isolated 6.66 grams (59%) of 2-methoxycarbonylaminopropionic acid methyl ester with a boiling point of 65°–67° C./0.0013 mbar.

$C_6H_{11}NO_4$ (161.16)

Calculated: C,44.72%; H,6.28%; N,8.69%.
Found: C,44.58%; H,6.84%; N,8.79%.

3.22 grams of the previously undescribed compound were saponified according to the process of Example 3. There were obtained 2.31 grams (92%) of D,L-alanine hydrochloride pure by thin layer chromatography.

EXAMPLE 10

13.65 grams of 2-bromobutyric acid ethyl ester were reacted with 8.52 grams of potassium cyanate and 11.29 grams of ethanol according to Example 1 to 2-ethoxycarbonylaminobutyric acid ethyl ester. The yield was 7.84 grams (55%), the boiling point 78°–80° C./0.04 mbar. 2.03 grams of the monourethane were saponified in 7.5 ml of the acid mixture set forth in Example 3. There were obtained 1.29 grams (92.4%) of α-aminobutyric acid hydrochloride.

EXAMPLE 11

14.64 grams of 2-bromo-4-methyl valeric acid methyl ester were brought to reaction with potassium cyanate and methanol in the manner described in Example 1 (using the same amounts of potassium cyanate and methanol as in Example 1), reaction time 1 hour and then worked up. There were obtained 9.39 grams (66%) of 2-methoxycarbonylamino-4-methyl valeric acid methyl ester with a boiling point of 100° C./0.0013 mbar.

$C_9H_{17}NO_4$ (203.24)

Calculated: C,53.19%; H,8.43%; N,6.89%.
Found: C,53.04%; H,8.54%; N,6.84%.

2.09 grams of this previously unknown compound were saponified with 7.7 ml of the acid mixture according to Example 3. There were obtained 1.57 grams (91.1%) of D,L-leucine hydrochloride.

EXAMPLE 12

A mixture of 5.2 grams of 2,4-dibromobutyric acid methyl ester, 4.87 grams of potassium cyanate and 4.49 grams of methanol were stirred in 40 ml of DMF for 60 minutes at 100° C. The product was worked up as in Example 7. There were isolated 2.32 grams (46.7%) of 2,4-bis-(methoxycarbonylamino)-butyric acid methyl ester.

$C_9H_{16}N_2O_6$ (284.24)

Calculated: C,43.55%; H,6.50%; N,11.29%.
Found: C,43.42%; H,6.24%; N,11.72%.

The saponification of 0.9 gram of the compound was carried out with 15 ml of the acid mixture according to Example 3 and gave 0.68 gram (98%) of 2,4-diaminobutyric acid dihydrochloride which is pure by thin layer chromatography.

EXAMPLE 13

5.48 grams of 2,5-dibromomovaleric acid methyl ester were heated with 4.87 grams of potassium cyanate and 4.49 grams of methanol in 40 ml of DMF for 7 hours at 100° C. After working up as described in Example 7 there took place the first liquid chromatographic separation with a running agent mixture methyl acetate/petroleum ether (1:1 by volume). There were obtained 4.0 grams (about 90%) of a mixture consisting of:

2,5-bis(methoxycarbonylamino)-valeric acid methyl ester (I) and N-methoxycarbonyl proline methyl ester (II) in the ratio of about 1:1.2.

The second chromlographic separation with ethyl acetate yielded:

I pure and II in greater than 95 percent purity.

I: $C_{10}H_{18}N_2O_6$ (262.27)

Calculated: C,45.80%; H,6.92%; N,10.68%.
Found: C,45.79%; H,6.86%; N,10.62%.

II. $C_8H_{13}NO_4$ (187.195)

Calculated: C,51.33%; H,7.00%; N,7.48%.
Found: C,50.49%; H,6.88%; N,7.60%.

The saponification of 0.1473 gram of the diurethane I with 15 ml of the acid mixture according to Example 3 led to 0.0905 gram (78.5%) of D,L-ornithine dihydrochloride which is thin layer chromatographically pure.

0.233 gram of the monourethane II was correspondingly saponified to 0.1775 gram (94.4%) of D,L-proline hydrochloride, which likewise is thin layer chromatographically pure.

EXAMPLE 14

12.78 grams of 2-bromo-6-chlorohexanoic acid methyl ester, 6.08 grams of potassium cyanate and 2.72 grams of methanol were heated under powerful stirring in 70 ml of DMF for 1 hour. The reaction mixture was worked up in the manner described in Example 1. There were obtained 6.29 grams (50.3%) of 6-chloro-2-methoxycarbonylaminohexanoic acid methyl ester with boiling point of 113° C./0.0026 mbar.

$C_9H_{16}ClNO_4$ (237.69)

Calculated: C,45,48%; H,6.79%; N,5.89%; Cl, 14.92%.

Found: C,44.88%; H,6.40%; N,5.54%; Cl,14.87%.

3.0 grams of this previously not described compound were saponified according to Example 3. There were obtained 2.29 grams (89.9%) of 2-amino-6-chlorohexanoic acid hydrochloride having a melting point of 159°-163° C.

EXAMPLE 15

12.78 grams of 2-bromo-6-chlorohexanoic acid methyl ester, 6.08 grams of potassium cyanate, 3.50 grams of methanol and 0.25 gram of hexamethyl guanidinium cyanate were heated in 70 ml of acetonitrile for 25 hours at 80° C. under strong stirring. The reaction mixture was worked up as described in Example 1. There were obtained 7.59 grams (60.7%) of 6-chloro-2-methoxy-carbonylaminohexanoic acid methyl ester which was saponified as in Example 14 to 2-amino-6-chlorohexanoic acid hydrochloride.

EXAMPLE 16

10.71 grams of monobromo acetic acid methyl ester, 8.52 grams of potassium cyanate and 7.85 grams of methanol were heated in 70 ml of DMF following the procedure of Example 1 gave 6.62 grams (64.3%) of methoxycarbonylamino acetic acid methyl ester having a boiling point of 67°-8° C./0.0013 mbar.

EXAMPLE 17

2.94 grams of methoxycarbonylamino acetic acid methyl ester were saponified in the manner described in Example 3. There were obtained 2.19 grams (98.2%) of glycin hydrochloride.

The entire disclosure of German priority application No. P 28 54 627.2-42 is hereby incorporated by reference.

What is claimed is:

1. A process for the production of an aminoacid hydrochlorides or a diaminoacide dihydrochlorides comprising reacting an ester of a halocarboxylic acid having the formula:

$$R'-CH_2-CH-COOR \text{ or} \quad (I)$$
$$| $$
$$Hal$$

-continued
$$Hal-(CH_2)_n-COOR \text{ or} \quad (II)$$
$$Hal-(CH_2)_m-CH-COOR \quad (III)$$
$$|$$
$$Hal$$

in which Hal is chlorine or bromine, R is methyl or ethyl, R' is hydrogen or an alkyl group with 1 to 6 carbon atoms, n is one or a whole number between 3 and 5 inclusive and m is a whole number between 2 and 4 inclusive, in an aprotic solvent at a temperature between 80° and 120° C. with an alkali metal cyanate of the formula MeOCN in which Me is lithium, sodium or potassium, and methanol or ethanol and subsequently saponifying the alkoxycarbonylaminocarboxylic acid ester or bis-(alkoxycarbonylamino)-carboxylic acid ester with a mixture of equal parts of concentrated hydrochloric acid, 100 weight percent formic acid and water at reflux temperature.

2. A process according to claim 1 wherein there is employed (III), m is 4 and there is obtained lysine.

3. A process according to claim 2 wherein both halogen atoms are bromine.

4. A process according to claim 1 wherein Hal is bromine.

5. A process according to claim 1 wherein there is employed (III), the Hal in the 2-position is bromine and the Hal in the omega position is chlorine.

6. A process according to claim 1 wherein Me is potassium.

7. A process according to claim 1 wherein the aprotic solvent is dimethyl sulfoxide, dimethylformamide or N-methyl pyrrolidone.

8. A process according to claim 7 wherein the reaction of the halocarboxylic acid ester with the alkali metal cyanate and the alcohol is carried out in the presence of tetraethyl ammonium cycanate or hexamethyl guanidinium cyanate as a catalyst.

9. A process according to claim 1 wherein the reaction of the halocarboxylic acid ester with the alkali metal cyanate and the alcohol is carried out in the presence of tetraethyl ammonium cyanate or hexamethyl guanidinium cyanate as a catalyst.

10. A process according to claim 9 comprising first isolating the alkoxycarbonylaminocarboxylic acid ester or bis-(alkoxycarbonylamino)-carboxylic acid ester intermediate in pure form and then saponifying the pure intermediate.

11. A process according to claim 1 comprising first isolating the alkoxycarbonylaminocarboxylic acid ester or bis-(alkoxycarbonylamino)-carboxylic acid ester intermediate in pure form and then saponifying the pure intermediate.

12. A process according to claim 1 comprising reducing the reaction time of the halocarboxylic acid ester with the alkali metal cyanate by adding an alkali metal bromide in an amount sufficient to reduce the reaction time.

13. The process of claim 12 wherein there is employed potassium bromide.

14. The process of claim 13 wherein the potassium bromide is employed in an amount of 0.5 to 1.5 moles per mole of alkali metal cyanate.

* * * * *